United States Patent [19]
Amstutz et al.

[11] Patent Number: 4,977,176
[45] Date of Patent: Dec. 11, 1990

[54] PILOCARPINE COMPOUNDS WHICH ARE USE AS PHARMACEUTICAL AGENTS

[75] Inventors: René Amstutz, Himmelried; Georg Bolliger, Binningen; Gideon Shapiro, Basel, all of Switzerland

[73] Assignee: Sandoz Ltd., Basel, Switzerland

[21] Appl. No.: 336,279

[22] Filed: Apr. 11, 1989

Related U.S. Application Data

[62] Division of Ser. No. 149,812, Jan. 29, 1988, Pat. No. 4,835,174.

[51] Int. Cl.⁵ .................. A61K 31/415; C07D 233/60
[52] U.S. Cl. ..................................... 514/397; 548/336
[58] Field of Search .......................... 548/336; 514/397

[56] References Cited

U.S. PATENT DOCUMENTS 4,581,369 4/1986 Tsuruda et al. ..................... 548/336

Primary Examiner—Mary C. Lee
Assistant Examiner—Zinna Northington-Davis
Attorney, Agent, or Firm—Gerald D. Sharkin; Robert S. Honor; Thomas O. McGovern

[57] ABSTRACT

Pilocarpine derivatives of formula I,

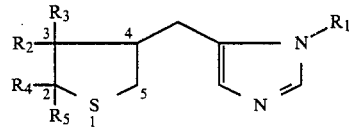

wherein $R_1$ to $R_5$ are as defined in the description, are useful in the treatment of senile dementia, Alzheimer's disease, confusional conditions in the elderly, myasthenia gravis, schizophrenia, mania or glaucoma.

18 Claims, No Drawings 4,977,176

PILOCARPINE COMPOUNDS WHICH ARE USE AS PHARMACEUTICAL AGENTS

This is a division of application Ser. No. 07/149,812, filed Jan. 29, 1988 which issued as U.S. Pat. No. 4,835,174 on May 30, 1989.

The present invention relates to new pilocarpine derivatives.

Pilocarpine is the generic name of (3S-cis)-3-ethyl-dihydro-4-[(1-methyl-1H-imidazol-5-yl)methyl]-2(3H)-furanone. Pilocarpine is known in the literature as a cholinergic agent. It has now surprisingly been found that the compound resulting from replacement of the furane ring by a thiophene ring, as well as derivatives of this compound, exhibit a particularly interesting pharmaceutical profile.

These new pilocarpine derivatives, hereinafter referred to as new compounds, comprise the compounds of formula I,

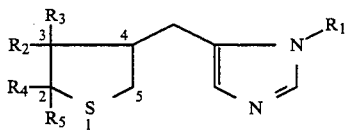

wherein
$R_1$ is $(C_{1-4})$alkyl,
$R_2$ and $R_3$ independently are hydrogen or $(C_{1-4})$alkyl,
$R_4$ and $R_5$ together are $=O$, $=S$ or $=NR$, wherein R is mono- or di$(C_{1-4})$alkylcarbamoyloxy, or
$R_4$ is hydrogen and
$R_5$ is hydrogen, hydroxy or $—OR'$, wherein R' is $(C_{1-4})$alkyl or mono- or di$(C_{1-4})$alkylcarbamoyl, in free base or acid addition salt form.

Depending on the substituents the new compounds may present asymmetrical carbon atoms in positions 2, 3 and 4. The invention includes all resulting cis/trans isomers, more generally all stereoisomers as well as their mixtures, e.g. the racemic mixtures of the enantiomers.

Any alkyl preferably has one or two carbon atoms.
$R_1$ preferably is methyl.
Preferably one of the substituents $R_2$ and $R_3$ is hydrogen and the other ethyl.
Preferably $R_4$ and $R_5$ together are $=O$.

In a group of compounds of formula I, $R_1$ is as defined above, $R_2$ is hydrogen, $R_3$ is ethyl and $R_4$ and $R_5$ together are $=O$ or $=S$.

The following significances are preferred:
$R_1$ is methyl;
One of the substituents $R_2$ and $R_3$ is hydrogen and the other is $(C_{1-4})$alkyl, particularly ethyl;
$R_4$ and $R_5$ together are $=O$ or $=S$, particularly $=O$.

The present invention also provides a process for the production of a compound of formula I or an acid addition salt thereof, which includes the step of reacting a compound of formula II,

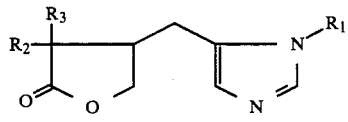

wherein $R_1$, $R_2$ and $R_3$ are as defined above, with a phosphorus sulfide, optionally converting a thus obtained compound of formula I, wherein $R_4$ and $R_5$ together are $=O$ or $=S$, into a further compound of formula I and recovering the resultant compound of formula I in free base or acid addition salt form.

The reaction of the compound of formula II with the phosphorus sulfide may take place in known manner, using for example $P_4S_{10}$ as phosphorus sulfide, or preferably the Lawesson's reagent of formula

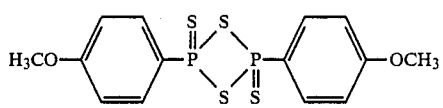

Working up of the reaction mixture may be effected in accordance with known methods. One obtains a mixture of a compound of formula I wherein $R_4$ and $R_5$ together are $=O$ with a compound of formula I wherein $R_4$ and $R_5$ together are $=S$. The separation may be effected using known methods, e.g. chromatographically.

The compounds of formula I wherein $R_4$ and $R_5$ together are $=O$ may also be prepared by reacting a compound of formula II with potassium thioacetate in known manner, e.g. as described in example 2 hereinafter.

The conversion of the compounds of formula I wherein $R_4$ and $R_5$ together are $=O$ or $=S$ into further compounds of formula I may be effected in accordance with known methods, e.g. as follows:

Compounds of formula I wherein $R_4$ is hydrogen and $R_5$ is hydroxy may be produced by reducing compounds of formula I wherein $R_4$ and $R_5$ together are $=O$, e.g. using diisobutylaluminium hydride, as described in example 4. The so obtained compounds may be converted into compounds of formula I wherein $R_4$ is hydrogen and $R_5$ is $—OR'$ by reaction with a compound of formula $R'OH$ (when R' is above defined alkyl) or of formula $R'Cl$ (when R' is above defined alkylcarbamoyl), as described in examples 5 and 6.

Compounds of formula I wherein $R_4$ and $R_5$ together are $=NR$ may be produced by reacting a compound wherein $R_4$ and $R_5$ together are $=S$ with hydroxylamine hydrochloride as described in example 7 and reacting the resultant compound with a mono- or dialkylaminocarboxylic acid chloride in analogy to example 6.

The compounds of formula I may be isolated in free form or in the form of their addition salts with acids. Acid addition salts can be produced from the free base forms in known manner, and vice versa.

The starting compounds of formula II are known or may be produced by known processes or in analogous manner to known processes. For example (3S-cis)-3-ethyldihydro-4-[(1-methyl-1H-imidazol-5-yl)methyl]-2(3H)-furanone [(+)-pilocarpine] is disclosed in the literature as a pharmaceutical and available on the market.

The compounds of formula I and their pharmaceutically acceptable acid addition salts, hereinafter referred to as compounds according to the invention, exhibit pharmacological activity and are, therefore, useful as pharmaceuticals.

In particular, the compounds according to the invention enhance cholinergic activity in the following tests:

Electrically Evoked Acetylcholine Release From Hippocampal Slices (Rat)

The compounds according to the invention at concentrations from about $10^{-6}$M to about $10^{-4}$M antagonize the inhibitory effects of muscarinic agonists such as oxotremorine on presynaptic muscarinic receptors, indicating that the compounds are presynaptic muscarinic antagonists. In addition, the compounds antagonize the inhibitory effect of endogenous acetylcholine which accumulates after release from nerve terminals in presence of the acetylcholine esterase inhibitor physostigmine.

Effects on the Electrical Activity of Cultured Hippocampal Pyramidal Cells

The compounds according to the invention at concentrations from about $10^{-6}$M to about $10^{-4}$M fail to influence the activity of pyramidal cells in an experimental situation with no cholinergic cells present, whereas they induce excitatory effects in co-cultures which contain functional cholinergic connectivities (co-culture prepared from septum and hippocampus). The results demonstrate that the presence of cholinergic cells is required for the compounds according to the invention to exert excitatory effects. The data are compatible with the view that the compounds according to the invention induce release of acetylcholine from cholinergic terminals, without blocking postsynaptic muscarinic receptors.

Passive Avoidance (Scopolamine Amnesia) in Mice

When mice are injected with scopolamine before one-trial passive avoidance training they appear to form no memory of the training, as indicated by their performance on a subsequent memory retention test. The compounds according to the invention partly reverse this impairment when also given before training. After oral administration the lowest dose producing significant improvement is 153 $\mu$mol/kg (40 mg/kg). The data indicate that the compounds according to the invention can improve cognitive impairment resulting from cholinergic hypofunction most likely by acting as presynaptic antagonists at receptors where acetylcholine acts to inhibit its own release.

Effects on Acetylcholine Concentration in Rat Brain

The compounds according to the invention after oral administration of dosages from about 1 mg/kg to about 10 mg/kg induced a dose dependent, long lasting reduction in acetylcholine content of striatum, hippocampus and cortex. This effects is similar but 10 times weaker than those produced by scopolamine, a pre- and postsynaptic muscarinic antagonist. The concomitant application of the compounds according to the invention with an acetylcholine esterase inhibitor show distinctly different effects on acetylcholine levels from the combination of the classical antagonist scopolamine according to the invention. This indicates that the compounds according to the invention are selective presynaptic antagonists without postsynaptic antagonistic properties.

In addition to the mentioned presynaptic antagonism the compounds according to the invention with cis configuration in C 3/C 4 also interact as agonists with muscarinic receptors located postsynaptically. This is demonstrated by the effects obtained with the classical pharmacological tests:

(a) isolated Guinea pig ileum preparation: where the effects of the compounds on the contraction of the muscle is measured isotonically in comparison with the effects of muscarine.

(b) isolated cervical ganglion preparation of the rat: muscarinic agonists induce a depolarisation in this isolated ganglion; the effects are compared to those obtained after muscarine.

The methods used were described in: J. M. Palacios et al., Europ. J. Pharmacol. 125, 45–62, (1986).

The substances mentioned show pD2 values between 5 and 6.5 in these tests and they can act as full or partial agonists.

The above results indicate that the compounds according to the invention act predominantly as presynaptic muscarinic antagonists and some of them as postsynaptic muscarinic agonists. Their ability to improve memory function which has been impaired by scopolamine indicate that the compounds according to the invention are useful in senile mental decline, senile dementia and Alzheimer's disease, especially in the early stages when a proportion of cholinergic nerve terminals are intact. In addition the compounds according to the invention are, therefore, useful in the therapy of confusional conditions in the elderly, myasthenia gravis, schizophrenia, mania and glaucoma.

For these indications, the appropriate dosage will, of course, vary depending upon, for example, the compound according to the invention employed, the host, the mode of administration and the nature and severity of the condition being treated. However, in general, satisfactory results in animals are indicated to be obtained at daily dosages from about 0.01 to about 10 mg/kg, e.g. about 0.1 to about 10 mg/kg animal body weight. In larger mammals, for example humans, an indicated daily dosage is in the range from about 1 to about 250 mg, e.g. about 1 to about 50 mg of a compound according to the invention, conveniently administered, for example, in divided doses up to four times a day.

The compounds according to the invention may be administered by any conventional route, in particular enterally, preferably orally, e.g. in the form of tablets or capsules, or parenterally, e.g. in the form of injectable solutions or suspensions.

The compound of example 2 is the preferred compound for the above mentioned indications. It has, for example, been determined that this compound induces a significant reduction of the acetylcholine concentration after 3 mg/kg p.o. in the cortex and after 1 mg/kg p.o. in the hippocampus and striatum of the rat. It is, therefore, indicated that for these indications the compound of example 2 may be administered at daily dosages of from 1 to 50 mg p.o. to larger mammals, for example humans. The preferred indication is senile dementia.

The present invention also provides pharmaceutical compositions comprising a compound according to the invention in association with at least one pharmaceutical carrier or diluent. Such compositions may be manufactured in conventional manner. Unit dosage forms contain, for example, from about 0.25 to about 125 mg of a compound according to the invention.

For the treatment of glaucoma an especially convenient mode of administration is in the form of an ophthalmic composition comprising the compound according to the invention in association with an ophthalmic carrier.

In the following examples, all temperatures are uncorrected and are in degrees Centigrade.

EXAMPLE 1

(+)-(3R-trans)-3-ethyldihydro-4-[(1-methyl-1H-imidazol-5-yl)methyl]-2(3H)-thiophenone and (−)-(3R-trans)-3-ethyldihydro-4-[(1-methyl-1H-imidazol-5-yl)methyl]-2(3H)-thiophene-thione 10 g of (+)-pilocarpine hydrochloride are suspended in 600 ml of xylene together with 24.8 g of Lawesson's reagent, and stirred for 7 hours at 135° under a nitrogen atmosphere in a 1.5 liters sulphonation flask having a gas feed pipe and reflux condenser. After cooling to room temperature, the xylene is decanted off and the resinous, brownish residue is dissolved in 400 ml of methylene chloride/methanol (95:5) and extracted twice with 150 ml of 2N soda solution. After drying the organic phase with sodium sulphate, the mixture is filtered and concentrated by evaporation.

The residue is chromatographed with 100 times the amount of silica gel, using methylene chloride/methanol/ammonia (93:7:0.7) as eluant.

(+)-(3R-trans)-3-ethyldihydro-4-[(1-methyl-1H-imidazol-5-yl)-methyl]-2(3H)-thiophenone-dihydrogen phosphate (from ethanol) melts at 189°–192°. $[\alpha]_D^{20} = +20.2°$ (c=1.0 in water).

The hydrochloride of (−)-(3R-trans)-3-ethyldihydro-4-[(1-methyl-1H-imidazol-5-yl)methyl-2(3H)-thiophene-thione (from methanol/ether) melts at 158°–161°. $[\alpha]_D^{20} = -23.6°$ (c=0.5 in ethanol).

EXAMPLE 2

(+)-(3S-cis)-3-ethyldihydro-4-[(1-methyl-1H-imidazol-5-yl)methyl]-2(3H)-thiophenone 39.7 g of potassium thioacetate are stirred for 6 hours at 150° together with 42.5 g of (+)-pilocarpine in 500 ml of dimethylformamide. After cooling and evaporating the solvent, the brown residue is dissolved in 1.5 liters of 95% methylene chloride/methanol, and is washed twice, with 200 ml of saturated sodium bicarbonate each time, and once with 200 ml of water. After drying the organic phase with sodium sulphate, the mixture is filtered and concentrated by evaporation.

The residue is chromatographed with 100 times the amount of silica gel, using methylene chloride/methanol/ammonia (97.5:2.5:0.3) as eluant.

The oil comprises a mixture of 80:20 trans:cis.

26.3 ml of butyllithium (1.6N in hexane) are added in drops at 0° under an argon atmosphere to a solution of 6.55 ml of diisopropylamine in 250 ml of absolute tetrahydrofuran. 7.0 g of the trans/cis mixture, dissolved in 60 ml of absolute tetrahydrofuran, are subsequently added dropwise to the lithiumdiisopropylamide which has been cooled to −70°. Stirring is effected for ½ hour at −70°, and then 15.6 g of di-t-butyl-hydroxy-toluene, dissolved in 70 ml of tetrahydrofuran, are added in drops. The cold solution is poured into 300 ml of 2N HCl and the aqueous phase is extracted twice with 500 ml of methylene chloride. The aqueous phase is adjusted to pH 8 with 2N sodium carbonate solution, and extracted three times with 250 ml of methylene chloride. The organic phase is dried with sodium sulphate, filtered and concentrated by evaporation.

Stereoisomerically pure cis is obtained by recrystallising the D(+)-toluyl tartrate from ethanol.

(+)-(3S-cis)-3-ethyldihydro-4-[(1-methyl-1H-imidazol-5-yl)methyl]-2(3H)-thiophenone dihydrogen phosphate (from ethanol) melts at 193°–196° (decomp.); $[\alpha]_D^{20} = +37.4°$ (c=0.65 in water).

EXAMPLE 3

The following compounds of formula I are produced analogously to example 1 or 2:

3a. (−)-dihydro-4-[(1-methyl-1H-imidazol-5-yl)methyl]-2(3H)-thiophenone M.p.=142°–145° (decomp.). $[\alpha]_D^{20} = -20.8°$ (c=0.73 in H₂O).

3b. (±)-3-ethyldihydro-3-methyl-4-[(1-methyl-1H-imidazol-5-yl)methyl]-2(3H)-thiophenone M.p.=195°–196° (decomp.)

EXAMPLE 4

(+)-(3R-trans)-3-ethyl-2-hydroxy-4-[(1-methyl-1H-imidazol-5-yl)methyl]-tetrahydrothiophene 17 ml (17 mmol) of diisobutylaluminium hydride (1.0M in hexane) are added to a solution of 2.7 g (12 mmol) of trans-thiopilocarpine in 30 ml of methylene chloride at −70° under an argon atmosphere. The solution is left to warm to 0° and 2 ml of saturated sodium sulphate solution are added, whereupon a white precipitate is formed. The solution is separated by suction and concentrated to an orange oil. The oil is chromatographed on 50 times the amount of silica gel, using methylene chloride/methanol/ammonia (89:10:1) as eluant. The product is reacted with one equivalent of fumaric acid and the resulting fumarate is recrystallised from ethanol-ether. The 360 Mhz ¹H NMR spectrum shows that the product is present as a 2:1 diastereoisomeric mixture at C2.

The fumarate of the title compound melts at 125°–127°. $[\alpha]_D^{20} = +85.2°$ (c 0.43 in H₂O).

EXAMPLE 4a (+)-(3S-cis)-3-ethyl-2-hydroxy-4-[(1-methyl-1H-imidazol-5-yl)methyl]-tetrahydrothiophene One proceeds analogously to example 4, using cis-thiopilocarpine. The hydrogen fumarate of the title compound melts at 110°–112° (decomp.). $[\alpha]_D^{20} = +38.3°$ (c=0.35 in H₂O).

EXAMPLE 5

(+)-(3S-cis)-3-ethyl-4-[(1-methyl-1H-imidazol-5-yl)methyl]-2-methoxy-tetrahydrothiophene 1.1 ml of ethanol are added at 60° to a solution of 3.0 g (13.3 mmol) of cis-thiopilocarpine lactol in 40 ml methylene chloride. 3.4 ml (27 mmol) of borotrifluoroetherate are then added and the reaction mixture is left to warm to room temperature and stirred overnight. 2N soda solution is added and the mixture is extracted with methylene chloride. The organic phases are dried over sodium sulphate and concentrated to a yellow resinous product. This product is chromatographed on silica gel using methylene chloride/methanol/ammonia (90:9:1) as eluant. The resulting product (2.8 g, 11.6 mmol) is reacted with one equivalent of oxalic acid and the resulting salt is recrystallised from ethanol-ether. NMR analysis shows that the product is present as a 90:10 diastereoisomeric mixture at C2.

The hydrogen oxalate of the title compound melts at 144°–148° (from ethanol-ether). $[\alpha]_D^{20} = +112°$ (c=0.47 in ethanol).

EXAMPLE 5a (+)-(3R-trans)-3-ethyl-4-[(1-methyl-1H-imidazol-5-yl)methyl]-2-methoxy-tetrahydrothiophene One proceeds analogously to example 5, using trans-thiopilocarpine lactol. The hydrogen oxalate of the title compound melts at 87°–89°. $[\alpha]_D^{20} = +19.7°$ (c=0.33 in ethanol).

EXAMPLE 6

(+)-(3R-trans)-3-ethyl-4-[(1-methyl-1H-imidazol-5-yl)methyl]-2-(N,N-dimethylcarbamoyloxy)-tetrahydrothiophene 2.7 ml of N,N-dimethylcarbamoyl chloride are added dropwise at room temperature to a solution of 2.7 g (12 mmol) of the compound of example 4, 0.4 ml (30 mmol) of triethylamine and 270 mg of dimethylaminopyridine in 25 ml of methylene chloride. The solution is stirred overnight and extracted with sodium bicarbonate. The organic phase is separated, dried over sodium sulphate and concentrated to an oil. The oil is chromatographed on silica gel using methylenechloride/methanol (97:3) as eluent. The resulting product (1.4 g; 4.7 mmol) is present as a 70:30 diastereoisomeric mixture at C2 according to NMR analysis.

The hydrogen fumarate of the title compound (from ethanol-ethyl acetate) melts at 134°–137°. $[\alpha]_D^{20} = +43.0°$ (c=0.5 in H₂O).

EXAMPLE 7

(−)-(3R-trans)-3-ethyldihydro-4-[(1-methyl-1H-imidazol-5-yl)methyl]-2-(N,N-dimethylcarbamoyloximino)-3H-thiophene (a) 5 ml 2N soda solution are added to a solution of 1.0 g (4.2 mmol) of (+)-(3R-trans)-3-ethyldihydro-4-[(1-methyl-1H-imidazol-5-yl)methyl]-2(3H)-thiophene-thione and 420 mg (6.0 mmol) of hydroxylamine hydrochloride in 13 ml of methanol. Stirring is effected overnight and methylene chloride and sodium bicarbonate are added. The organic phase is dried over sodium sulphate and concentrated. The resulting oil is chromatographed on silica gel using methylene chloride/methanol/ammonia (90:9:1) as eluent.

(b) The (+)-(3R-trans)-3-ethyldihydro-4-[(1-methyl-1H-imidazol-5-yl)methyl]-2-oximino-3H-thiophen obtained under a) is converted into the title compound analogously to example 6. The hydrogen fumarate melts at 123°–127° (decomp.). $[\alpha]_D^{20} = -3.0°$ (c=1.0 in H₂O).

What we claim is:

1. A method of treating confusional conditions in the elderly, myasthenia gravis, schizophrenia, mania or glaucoma in a subject in need of such treatment, which comprises administering a therapeutically effective amount of a compound of formula I:

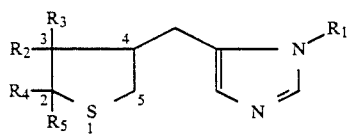

wherein
R₁ is (C₁₋₄)alkyl,
R₂ and R₃ independently are hydrogen or (C₁₋₄)alkyl,
R₄ and R₅ together are =O, =S or =NR, wherein R is mono- or di(C₁₋₄)alkylcarbamoyloxy, or
R₄ is hydrogen and
R₅ is hydrogen, hydroxy or —OR′, wherein R′ is (C₁₋₄)alkyl or mono- or di(C₁₋₄)alkylcarbamoyl, in free base or acid addition salt form.

2. A method according to claim 1 of treating confusional conditions in the elderly.

3. A method according to claim 1 wherein
R₁ is (C₁₋₄)alkyl,
R₂ is hydrogen,
R₃ is ethyl and
R₄ and R₅ together are =O or =S,
in free base or acid addition salt form.

4. A method according to claim 1 wherein
R₁ is methyl,
R₂ is hydrogen,
R₃ is (C₁₋₄)alkyl,
R₄ and R₅ together are =O or =S.

5. A method according to claim 1, in which 1 to 250 mg. of the compound is administered daily.

6. A method according to claim 1, in which 1 to 50 mg. of the compound is administered daily.

7. A method according to claim 1, in which 0.25 to 125 mg. of the compound is administered per unit dose.

8. The method according to claim 1, in which the compound is (+)-(3S-cis)-3-ethyldihydro-4-[(1-methyl-1H-imidazol-5-yl)methyl]-2(3H)-thiophenone in free base or acid addition salt form.

9. The method according to claim 1, in which the compound is (+)-(3R-trans)-3-ethyldihydro-4-[(1-methyl-1H-imidazol-5-yl)methyl]-2(3H)-thiophenone in free base or acid addition salt form.

10. The method according to claim 1, in which the compound is (−)-(3R-trans)-3-ethyldihydro-4-[(1-methyl-1H-imidazol-5-yl)methyl]-2(3H)-thiophene-thione in free base or acid addition salt form.

11. The method according to claim 1, in which the compound is (−)-dihydro-4-[(1-methyl-1H-imidazol-5-yl)methyl]-2(3H)-thiophenone in free base or acid addition salt form.

12. The method according to claim 1, in which the compound is (±)-3-ethyldihydro-3-methyl-4-[(1-methyl-1H-imidazol-5-yl)methyl]-2(3H)-thiophenone in free base or acid addition salt form.

13. The method according to claim 1, in which the compound is (+)-(3R-trans)-3-ethyl-2-hydroxy-4-[(1-methyl-1H-imidazol-5-yl)methyl]-tetrahydrothiophene in free base or acid addition salt form.

14. The method according to claim 1, in which the compound is (+)-(3S-cis)-3-ethyl-2-hydroxy-4-[(1-methyl-1H-imidazol-5-yl)methyl]-tetrahydrothiophene in free base or acid addition salt form.

15. The method according to claim 1, in which the compound is (+)-(3S-cis)-3-ethyl-4-[(1-methyl-1H-imidazol-5-yl)methyl]-2-methoxy-tetrahydrothiophene in free base or acid addition salt form.

16. The method according to claim 1, in which the compound is (+)-(3R-trans)-3-ethyl-4-[(1-methyl-1H-imidazol-5-yl)methyl]-2-methoxy-tetrahydrothiophene in free base or acid addition salt form.

17. The method according to claim 1, in which the compound is (+)-(3R-trans)-3-ethyl-4-[(1-methyl-1H-imidazol-5-yl)methyl]-2-(N,N-dimethylcarbamoyloxy)-tetrahydrothiophene in free base or acid addition salt form.

18. The method according to claim 1, in which the compound is (−)-(3R-trans)-3-ethyldihydro-4-[(1-methyl-1H-imidazol-5-yl)methyl]-2-(N,N-dimethylcarbamoyl-oximino)-3H-thiophene in free base or acid addition salt form.

* * * * *